United States Patent [19]

Takei et al.

[11] Patent Number: 5,679,821
[45] Date of Patent: Oct. 21, 1997

[54] PROCESS FOR PREPARING ORGANOSILICON COMPOUND

[75] Inventors: Masao Takei; Akira Sumi; Kaoru Kimura, all of Aichi, Japan

[73] Assignee: Toagosei Co., Ltd., Tokyo, Japan

[21] Appl. No.: 789,137

[22] Filed: Jan. 28, 1997

[30] Foreign Application Priority Data

Feb. 1, 1996 [JP] Japan ................... 8-039027

[51] Int. Cl.$^6$ ................... C07F 7/08; C07F 7/18
[52] U.S. Cl. ................... 556/438
[58] Field of Search ................... 556/438

[56] References Cited

U.S. PATENT DOCUMENTS

| | | | |
|---|---|---|---|
| 3,099,670 | 7/1963 | Prober | 556/438 |
| 3,109,011 | 10/1963 | Pike et al. | 556/438 |
| 4,709,067 | 11/1987 | Chu et al. | |
| 5,508,459 | 4/1996 | Arai et al. | 556/438 |

*Primary Examiner*—Paul F. Shaver
*Attorney, Agent, or Firm*—Sughrue, Mion, Zinn, Macpeak & Seas, PLLC

[57] ABSTRACT

A process for the preparation of an organosilicon compound represented by formula (3):

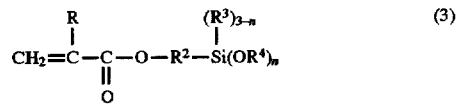

which process comprises reacting an organosilicon compound represented by formula (1) with a (meth)acrylic acid ester represented by formula (2) in the presence of a catalyst:

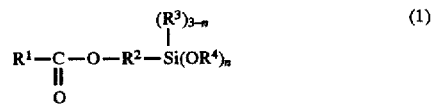

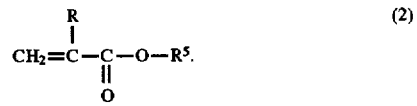

The symbols in the above formulae are defined in the specification.

6 Claims, No Drawings

PROCESS FOR PREPARING ORGANOSILICON COMPOUND

FIELD OF THE INVENTION

The present invention relates to a novel process by which an organosilicon compound represented by the following formula (3) can be readily prepared in a high yield. The organosilicon compound obtained is useful as, e.g., a silane coupling agent or a starting material for a reactive polymer.

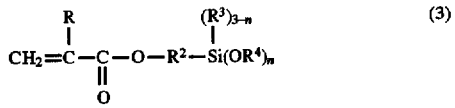

wherein R represents a hydrogen atom or a methyl group, $R^2$ represents an alkylene group having from 2 to 10 carbon atoms, $R^3$ and $R^4$ each represents an alkyl group having from 1 to 10 carbon atoms, and n represents an integer of 1, 2 or 3, provided that when a plurality of $R^3$ or $R^4$ groups are present, the plural groups may be the same or different from one another.

BACKGROUND OF THE INVENTION

The following three processes are known as conventional techniques for synthesizing an organosilicon compound represented by formula (3) shown above.

1) A process comprising reacting a metal salt of an acrylic acid with a chloroalkylsilane with elimination of a salt to obtain the organosilicon compound as disclosed in JP-B-42-23332 (the term "JP-B" as used herein means an "examined Japanese patent publication"), JP-A-52-73826 (the term "JP-A" as used herein means an "unexamined published Japanese patent application") and JP-A-3-209388.
2) A process comprising reacting an acrylic acid with a halogenoalkylsilane in the presence of a tertiary amine compound having a cyclic structure to obtain the organosilicon compound as disclosed in JP-A-5-306290.
3) A process comprising subjecting a compound having an unsaturated double bond, e.g., allyl acrylate, and a hydrosilane to a hydrosilylation reaction in the presence of a transition metal catalyst to obtain the organosilicon compound as disclosed in JP-B-38-2136.

However, process 1) is disadvantageous in that the metal salt of an acrylic acid used in the reaction is difficult to handle because it is solid, and that the process is very troublesome because it necessitates a step for salt removal.

Process 2) is disadvantageous in that since the reaction yields a hydrogen halide as a by-product, the production equipment is apt to corrode.

Further, process 3) is disadvantageous in that the unsaturated starting material, i.e., allyl acrylate or the like, is expensive because it is unstable and difficult to produce, and that the hydrosilane shows poor addition selectivity in the hydrosilylation reaction, resulting in a low yield.

The present invention has been achieved to solve the above described problems in conventional techniques.

SUMMARY OF THE INVENTION

Therefore, an object of the present invention is to provide a novel process capable of readily preparing an organosilicon compound in a high yield from starting materials which are inexpensive and easy to handle.

Other objects and effects of the present invention will be apparent from the following description.

As a result of extensive studies made by the present inventors in order to accomplish the above objects, the present invention has been achieved.

The present invention relates a process for the preparation of an organosilicon compound represented by formula (3):

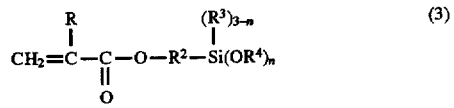

wherein R represents a hydrogen atom or a methyl group; $R^2$ represents an alkylene group having from 2 to 10 carbon atoms; $R^3$ and $R^4$ each represents an alkyl group having from 1 to 10 carbon atoms; and n represents an integer of 1, 2 or 3, provided that when a plurality of $R^3$ or $R^4$ groups are present, the plural groups may be the same or different from one another, which process comprises reacting an organosilicon compound represented by formula (1) with a (meth)acrylic acid ester represented by formula (2) in the presence of a catalyst:

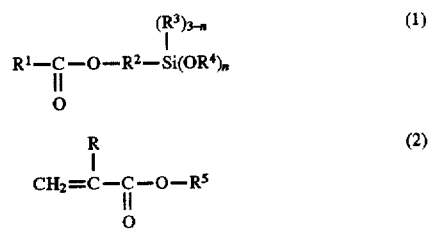

wherein $R^1$ represents an alkyl group having from 1 to 10 carbon atoms; $R^2$, $R^3$, $R^4$, n and R have the same meaning as that defined above, respectively; $R^5$ represents an alkyl or cycloalkyl group having from 2 to 20 carbon atoms.

DETAILED DESCRIPTION OF THE INVENTION

In formula (1), $R^1$ preferably represents an alkyl group having from 1 or 2 carbon atoms, $R^3$ preferably represents an alkyl group having from 1 to 3 carbon atoms, and $R^4$ preferably represents an alkyl group having from 1 to 3 carbon atoms.

Examples of the organosilicon compound represented by formula (1) (hereinafter referred to as "compound (1)") for use in the present invention include trimethoxysilylpropyl acetate, triethoxysilylpropyl acetate, tripropoxysilylpropyl acetate, tributoxysilylpropyl acetate, dimethoxymethylsilylpropyl acetate, dimethylmethoxysilylpropyl acetate, diethoxymethylsilylpropyl acetate, dimethylethoxysilylpropyl acetate, trimethoxysilylpropyl propionate, triethoxysilylpropyl propionate, diethoxymethylsilylpropyl propionate, trimethoxysilylpropyl butyrate, triethoxysilylpropyl butyrate, trimethoxysilylpropyl valerate, triethoxysilylpropyl valerate, triethoxysilylpropyl 2-methylbutyrate, trimethoxysilylpropyl octanoate, triethoxysilylpropyl octanoate, trimethoxysilylpropyl nonanoate, triethoxysilylpropyl nonanoate, trimethoxysilylpropyl undecanoate and triethoxysilylpropyl undecanoate.

Preferred of these are trimethoxysilylpropyl acetate and triethoxysilylpropyl acetate from the standpoints of easiness of the separation thereof from the objective compound after reaction, etc.

Compound (1) can be easily produced at low cost. A typical process for synthesizing compound (1) comprises subjecting an alkyl allyl ester represented by the following formula (4) and a hydrosilane represented by the following formula (5) to a hydrosilylation reaction in the presence of a transition metal catalyst such as platinum, rhodium and palladium:

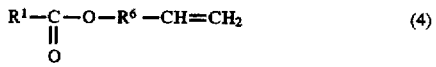 (4)

wherein $R^1$ represents an alkyl group having from 1 to 10 carbon atoms, and $R^6$ represents an alkylene group having from 2 to 8 carbon atoms;

 (5)

wherein $R^3$ and $R^4$ each represents an alkyl group having from 1 to 10 carbon atoms, and n represents an integer of 1, 2 or 3, provided that when a plurality of $R^3$ or $R^4$ groups are present, the plural groups may be the same or different from one another.

Examples of the (meth)acrylic acid ester represented by formula (2) (hereinafter referred to as "compound (2)") for use in the present invention include ethyl (meth)acrylate, propyl (meth)acrylate, butyl (meth)acrylate, pentyl (meth) acrylate, hexyl (meth)acrylate, heptyl (meth)acrylate, octyl (meth)acrylate, nonyl (meth)acrylate and lauryl (meth) acrylate.

Compound (2) is preferably an alkyl acrylate. Preferred examples thereof include ethyl acrylate, propyl acrylate, butyl acrylate, pentyl acrylate, hexyl acrylate, heptyl acrylate, octyl acrylate, nonyl acrylate and lauryl acrylate.

Further, $R^5$ in formula (2) is preferably an alkyl group having from 2 to 5 carbon atoms. Moreover, $R^5$ is preferably the same alkyl group as $R^4$ in formula (1) representing compound (1).

Compound (2) can be a commercial product on the general market. If desired and necessary, the compound may be dehydrated prior to use with a dehydrating agent such as, e.g., sodium sulfate, magnesium sulfate, or a molecular sieve.

The catalyst for use in the present invention is not particularly limited as long as it is capable of catalyzing transesterification. Examples thereof include $Ti(OEt)_4$, $Ti(OBu)_4$, $Ti(OPr)_4$, SnO, $Sn(COO)_2$, $Bu_2SnO$, $Bi(OH)_3$, $Zn(CH_3COO)_2 \cdot 2H_2O$, $Pb(CH_3COO)_2 \cdot 3H_2O$, $Pb(C_6H_5COO)_2 \cdot H_2O$, PbO, $Sb_2O_3$, $Al(CH_3COO)_3$, $Mn(CH_3COO)_2 \cdot 4H_2O$, $Co(CH_3COO)_2 \cdot 4H_2O$, $Cd(CH_3COO)_2$, $Cd(COO)_2$, and organometallic catalysts such as dibutyltin dilaurate, dibutyltin dimaleate, dibutyltin thiocarboxylates, dioctyltin mercaptide, stannous octoate and lead octenoate. Examples thereof further include triethylenediamine, tetramethylguanidine, 2-(dimethylaminomethyl)phenol, N,N,N',N'-tetramethylhexane-1,6-diamine, 1,8-diazabicyclo[5.4.0]undecene-7 and p-toluenesulfonic acid.

Of these catalysts, titanium alkoxides and p-toluenesulfonic acid are preferred from the standpoints of solubility in the starting materials, etc. In particular, titanium alkoxides are preferred.

In the present invention, the starting materials are used in such a molar proportion that the amount of compound (2) is preferably from 0.1 to 50 mol, more preferably from 0.5 to 10 mol, per mol of compound (1). The use amount of the catalyst is preferably from 0.001 to 0.5 mol, more preferably from 0.01 to 0.1 mol, per mol of compound (1).

Reaction conditions in the present invention vary depending on the kind and amount of compound (2) used and on the kind and amount of the catalyst used. However, in general, the reaction is preferably conducted at a temperature of from 30° to 180° C. for a period of from 0.5 to 24 hours.

Various organic solvents can be used for the reaction if desired and necessary. Examples thereof include aromatic solvents such as benzene, toluene and xylene, chlorinated solvents such as methylene chloride and chloroform, and alcohol solvents such as methanol and ethanol.

For preventing the (meth)acryloyl group from undergoing polymerization during the reaction, conventionally known various polymerization inhibitors may be added. Examples thereof include phenol compounds represented by methoxyphenol and 2,6-di-tert-butyl-4-methylphenol, quinone compounds represented by hydroquinone and anthraquinone, nitro compounds represented by m-dinitrobenzene, nitroso compounds represented by nitrosobenzene, amino compounds represented by methylaniline, organosulfur compounds represented by dithiobenzoyl disulfide and phenothiazine, and inorganic salts represented by cupric chloride and ferric chloride.

Such a polymerization inhibitor may be used in an amount of preferably from 1 ppm to 5% by weight based on the amount of compound (2). Furthermore, the content of the polymerization inhibitor in the final product is preferably from 100 to 2,000 ppm. Accordingly, it is preferred that purification of the reaction product and/or the addition of the polymerization inhibitor be conducted so that the content of the polymerization inhibitor in the final product is adjusted to the above described range.

The organosilicon compound obtained by the process of the present invention can be isolated and purified by ordinary means such as, for example, distillation, extraction, recrystallization, and column chromatography.

The present invention will be described below in more detail with reference to the following Examples and Comparative Example, but the invention should not be construed as being limited thereto.

REFERENCE SYNTHESIS EXAMPLE

This Example shows a synthesis of triethoxysilylpropyl acetate as a typical example of compound (1) for use as a starting material.

Into a 200-ml four-necked glass flask equipped with a thermometer, condenser, stirrer, and dropping funnel were introduced 46.0 g (0.46 mol) of allyl acetate and 184 μl of a 0.05M benzonitrile solution of $H_2PtCl_6 \cdot 6H_2O$. The contents were heated to 60° C., followed by dropwise addition of 75.6 g (0.46 mol) of triethoxysilane thereto over a period of 30 minutes. Thereafter, the mixture was reacted at 60° C. for 3 hours. The reaction product was purified by vacuum distillation (88° to 85° C./2 mmHg). Thus, triethoxysilylpropyl acetate as the objective compound was obtained in a yield of 89.2% (purity determined by gas chromatography, 99.3%).

Example 1

Into a 100-ml three-necked glass flask equipped with a thermometer and a condenser were introduced 10.0 g (0.038 mol) of triethoxysilylpropyl acetate, 38.0 g (0.38 mol) of ethyl acrylate and 0.2 g of $Ti(OBu)_4$. The resulting mixture was reacted at 100° C. for 6 hours.

After completion of the reaction, the reaction product was analyzed by gas chromatography (hereinafter referred to as GC). As a result, it was thus found that triethoxysilylpropyl acrylate as the objective compound had been obtained in a yield of 92% (in terms of triethoxysilylpropyl acetate).

NMR data for the triethoxysilylpropyl acrylate obtained are as follows (solvent, deuterio chloroform; internal reference, TMS).

δ (ppm)

0.52 to 0.84 (m, 2H), 1.27 (t, 9H), 1.58–1.90 (m, 2H), 3.84 (q, 6H), 4.16 (t, 2H), 5.74–6.57 (m, 3H).

Example 2

The same procedure as in Example 1 was followed to conduct a reaction, except that Ti(OEt)$_4$ was used in place of Ti(OBu)$_4$. After completion of the reaction, the reaction product was analyzed by GC. As a result, it was thus found that triethoxysilylpropyl acrylate as the objective compound had been obtained in a yield of 95% (in terms of triethoxysilylpropyl acetate).

Example 3

The same procedure as in Example 1 was followed to conduct a reaction, except that p-toluenesulfonic acid was used in place of Ti(OBu)$_4$. After completion of the reaction, the reaction product was analyzed by GC. As a result, it was thus found that triethoxysilylpropyl acrylate as the objective compound had been obtained in a yield of 41% (in terms of triethoxysilylpropyl acetate).

Example 4

The same procedure as in Example 1 was followed to conduct a reaction, except that 10.7 g (0.038 mol) of triethoxysilylpropyl propionate was used in place of 10.0 g (0.038 mol) of triethoxysilylpropyl acetate. After completion of the reaction, the reaction product was analyzed by GC. As a result, it was thus found that triethoxysilylpropyl acrylate as the objective compound had been obtained in a yield of 88% (in terms of triethoxysilylpropyl propionate).

Example 5

The same procedure as in Example 1 was followed to conduct a reaction, except that 0.02 g of methoxyphenol was further added. After completion of the reaction, the reaction product was analyzed by GC. As a result, it was thus found that triethoxysilylpropyl acrylate as the objective compound had been obtained in a yield of 96% (in terms of triethoxysilylpropyl acetate).

COMPARATIVE EXAMPLE

The same procedure as in Example 1 was followed to conduct a reaction, except that Ti(OBu)$_4$ was omitted. After completion of the reaction, the reaction product was analyzed by GC. As a result, it was found that triethoxysilylpropyl acrylate as the objective compound had not been obtained and the chromatogram data showed only the peak attributed to triethoxysilylpropyl acetate which was used as a starting material.

According to the process of the present invention, an objective organosilicon compound can be readily prepared in a high yield. Therefore, the efficiency of the production of the organosilicon compound, which is useful as, e.g., a silane coupling agent or a starting material for a reactive polymer, can be raised. Consequently, the process of the present invention is of great industrial value.

While the invention has been described in detail and with reference to specific examples thereof, it will be apparent to one skilled in the art that various changes and modifications can be made therein without departing from the spirit and scope thereof.

What is claimed is:

1. A process for the preparation of an organosilicon compound represented by formula (3):

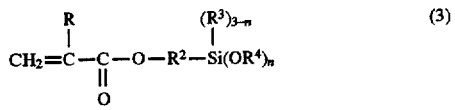

wherein R represents a hydrogen atom or a methyl group; R$^2$ represents an alkylene group having from 2 to 10 carbon atoms; R$^3$ and R$^4$ each represents an alkyl group having from 1 to 10 carbon atoms; and n represents an integer of 1, 2 or 3, provided that when a plurality of R$^3$ or R$^4$ groups are present, the plural groups may be the same or different from one another, which process comprises reacting an organosilicon compound represented by formula (1) with a (meth)acrylic acid ester represented by formula (2) in the presence of a catalyst:

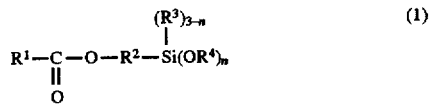

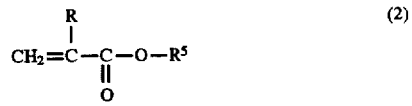

wherein R$^1$ represents an alkyl group having from 1 to 10 carbon atoms; R$^2$, R$^3$, R$^4$, n and R have the same meaning as that defined above, respectively; R$^5$ represents an alkyl or cycloalkyl group having from 2 to 20 carbon atoms.

2. The process of claim 1, wherein the catalyst comprises a titanium alkoxide.

3. The process of claim 1, wherein in formula (1), R$^2$ is a trimethylene group, R$^4$ is a methyl or ethyl group, and n is 3.

4. The process of claim 2, wherein in formula (1), R$^2$ is a trimethylene group, R$^4$ is a methyl or ethyl group, and n is 3.

5. The process of claim 1, wherein the (meth)acrylic acid ester represented by formula (2) is an alkyl acrylate.

6. The process of claim 5, wherein the alkyl acrylate represented by formula (2) is one selected from the group consisting of ethyl acrylate, propyl acrylate, butyl acrylate, pentyl acrylate, hexyl acrylate, heptyl acrylate, octyl acrylate, nonyl acrylate and lauryl acrylate.

* * * * *